US006586015B1

United States Patent
Gebhardt et al.

(10) Patent No.: US 6,586,015 B1
(45) Date of Patent: Jul. 1, 2003

(54) USE OF PHYLLANTHUS FOR TREATING CHRONIC INFLAMMATORY AND FIBROTIC PROCESSES

(75) Inventors: Rolf Gebhardt, Leipzig (DE); Angelika M. Vollmar, München (DE); Michael P. Manns, Isernhagen (DE); Matthias Bahr, Burgdorf (DE); Hildebert Wagner, Breitbrunn (DE); Gayane Hrachia Buniatian, Leipzig (DE)

(73) Assignee: Phytrix AG, Munich (DE)

( * ) Notice: Subject to any disclaimer, the term of this patent is extended or adjusted under 35 U.S.C. 154(b) by 0 days.

(21) Appl. No.: 09/560,557

(22) Filed: Apr. 28, 2000

(30) Foreign Application Priority Data

Apr. 29, 1999 (DE) .......................................... 199 19 585

(51) Int. Cl.$^7$ ............................................. A61K 35/78
(52) U.S. Cl. ...................... 424/725; 424/773; 424/774; 424/775; 424/976; 424/777; 424/778; 424/779
(58) Field of Search ............................... 424/725, 773, 424/774, 775, 776, 777, 778, 779

(56) References Cited

U.S. PATENT DOCUMENTS

| | | |
|---|---|---|
| 4,388,457 A | 6/1983 | Pettit |
| 4,673,575 A | 6/1987 | Venkateswaran et al. |
| 4,937,074 A | 6/1990 | Venkateswaran et al. |
| 5,529,778 A * | 6/1996 | Rohatgi |
| 5,571,441 A | 11/1996 | Andon et al. |
| 5,648,089 A | 7/1997 | Shawkat |
| 5,854,233 A * | 12/1998 | McLean |
| 6,136,316 A | 10/2000 | Mehrotra et al. |

FOREIGN PATENT DOCUMENTS

| | | |
|---|---|---|
| EP | 0903148 | 3/1999 |
| WO | 9740176 | 10/1997 |
| WO | WO 0061161 | 10/2000 |

OTHER PUBLICATIONS

Wang et al. J. of Lab. and Clinical Medicine (1995), vol. 126, pp. 350–352.*

Ihantola–Vormisto et al., Plant Medica (Dec. 1997), 63(6): 518–524. Anti–inflammatory activity of extracts from leaves of *Phyllanthus emblica*.

Thabrew et al., J of Ethnopharmacology (1991), 33(1–2): 63–66. Immunomodulatory activity of three Sri–Lankan medicinal plants used in hepatic disorders.

Paya et al., Phytotherapy Research (1996), 10: 228–232. Inhibitory effects of various extracts of Argentine plant species on free–radical–mediated reactions and human neutrophil functions.

International Search Report, WIPO, Application No. PCT/EP00/03869, completed Aug. 4, 2000, mailed Aug. 17, 2000 (English).

International Search Report, WIPO, Application No. PCT/EP00/03870, completed Aug. 9, 2000, mailed Aug. 24, 2000 (English).

Hagers Handbuch der Pharmazeutischen Praxis, 5. Ed., Folgeband 3, Drogen L–Z, Springer Verlag, Heidelberg 1998, pp. 338–352.

Xia Quan et al., "Ethnopharmacology of *Phyllanthus emblica* L.," *Zhongguo Zhongyao Zazhi*, 22(9):515–518, 525, 574; 1997. Abstract from Database Biosis 'Online! Biosciences Information Service, Philadelphia, PA, US.

Suresh et al., "Augmentation of murine natural killer cell and antibody dependent cellular cytotoxicity activities by *Phyllanthus emblica*, a new immunomodulator," *J Ethnopharmacol*, 44(1):55–60, Aug. 1994. Abstract from Database Biosis 'Online! Biosciences Information Service, Philadelphia, PA, US.

Calixto et al., "Antispasmodic effects of an alkaloid extracted from *Phyllanthus sellowianus*: a comparative study with papaverine," *Braz J Med Biol Res*, 17(3–4):313–21, 1984. Abstract from National Library of Medicine: IGM Full Record Screen.

Shanmugasundaram et al., "Anna Pavala Sindhooram—an antiatherosclerotic Indian drug," *J Ethnopharmacol*, 7(3):247–65, May 1983. Abstract from National Library of Medicine: IGM Full Record Screen.

Unander et al., "Uses and bioassays in Phyllanthus (Euphorbiaceae):a compilation II. The subgenus Phyllanthus," Journal of Ethnopharmacology, 34: 97–133, 1991.

Lee et al., "Regulation of Hepatitis B Virus Replication and Gene Expression by an Extract from *Phyllanthus Niruri*," AASLD Abstracts p. 117A, (#241) *Hepatology*, vol. 18, No. 4, Pt. 2, 1993.

Chintalwar et al., "An immunologically active arabinogalactan from *Tinospora cordifolia*," *Phytochemistry* 52:1089–1093, 1999.

Matthée et al., "HIV Reverse Transcriptase Inhibitors of Natural Origin," *Planta Medica* 65:493–506, 1999.

*Neueste Literatur zu Polysacchariden mit Immunstimulierender Wirkung*, Chapters in Immunomodulatory Agents from Plants, by H. Wagner (editor), Birkhäuser Verlag Basel–Boston–Berlin, 1999, pp. 1–39; 89–104; 161–201; 203–221; 325–356.

Zhou Shiwen Xu Chuanfu et al., "Mechanism of protective action of *Phyllanthus urinaria* L. against injuries of liver cells," *Zhongguo Zhongyao Zazhi*, 22(2):109–111, 129; 1997. Abstract from Datenbank BIOSIS bei STN:AN 1997:211857 BIOSIS, DN PREV 199799511060.

(List continued on next page.)

Primary Examiner—Leon B. Lankford, Jr.
Assistant Examiner—Susan D. Coe
(74) Attorney, Agent, or Firm—Baker Botts L.L.P.

(57) ABSTRACT

The present invention relates to the use of Phyllanthus for preventing or treating connective tissue proliferations, for maintaining the level of reduced glutathione, for inhibiting lipopolysaccharide (LPS)-induced nitric oxide synthase (NOS) and for inhibiting expression of the cyclooxygenase (COX-2) protein.

37 Claims, 12 Drawing Sheets

OTHER PUBLICATIONS

Asha et al., "Preliminary evaluation of the antihepatotoxic activity of *Phyllanthus kozhikodianus, P. maderaspatensis* and *Solanum indicum,*" *Fitoterapia*, 69(3):255–259, 1998. Abstract from Database Biosis Online Biosciences Information Service, Philadelphia, PA, US; 1998.

Jeena et al., "Effect of *Emblica officinalis, Phyllanthus amarus* and *Picrorrhiza kurroa* on N–nitrosodiethylamine induced hepatocarcinogenesis," *Cancer Letters*, 136(1):11–16, 1999. Abstract from Database Biosis 'Online! Biosciences Information Service, Philadelphia, PA, US; Feb. 8, 1999.

Hu et al., "Process for preparing *Gynostemma pentaphylla* throat–moistening tablets—useful for treating bronchitis, asthma, and cancer." Abstract form Chemical Patents Index, Documentation Abstracts Journal Derwent Publications, London: 19.3.99,Nr.99–081999/08 zu: CN 1194857–A.

Nippon Mektron KK (assignee), "Lipid metabolism improving and liver disturbance inhibitory agents—comprise organic solvent or water extract of Euphorbiaceae family, *Phyllanthus niruri*." Abstract from Chemical Patents Index, Documentation Abstracts Journal Derwent Publications, London: 19.12.97,Nr.97–508797/47 zu: JP 09241176 A.

Hou et al., "SOD prepared from *phyllanthus emblica* used as health food additives." Abstract from Chemical Patents Index, Documentation Abstracts Journal Derwent Publications, London: 12.12.97,Nr.97–490386/46 zu: CN 1121783 A.

Mikimoto Seiyaku KK (assignee), "Cosmetic material having good skin–moisturising effect—consists of compounded mixt. of cholesteric liq. crystal and one or more of e.g. *Piper longum, P. chaba* etc." Abstract from Chemical Patents Index, Documentation Abstracts Journal Derwent Publications, London: 29.9.95,Nr.95–252224/33 zu: JP 07157420 A.

Mikimoto Seiyaku KK (assignee), "Antioxidants used in lotions, creams and emulsions—contain solvent extract from e.g. *nigella savia, munronia pumila* or *borrelia hispida*." Abstract from Chemical Patents Index, Documentation Abstracts Journal Derwent Publications, London: 8.9.95, Nr.95–228590/30 zu: JP 07138126 A.

Cao et al., "Antioxidant for cosmetic products." Abstract from Chemical Patent Index, Documentation Abstracts Journal Derwent Publications, London: 8.9.95,Nr.95–224715/30 zu: CN 1086532 A.

Xiao et al., "Extraction of *Phyllanthus emblica* polysaccharides (PePS) and its scavenging effect on oxygen radical," *Zhongguo Yaoxue Zazhi (Beijing)*, 33(5):279–281, 1998. Abstract form Chemical Abstracts 130:452b.

Joy et al., "Inhibition of *Phyllanthus amarus* hepatocarcinogenesis induced by N–nitrosodiethylamine," *Journal of Clinical Biochemistry and Nutrition*, 24(3):133–139, 1998. Abstract from Datenbank BIOSIS bei STN:AN 1999:13953 BIOSIS, DN PREV 199900013953.

Potturi et al., "Protective effect of *Phyllanthus fraternus* against thioacetamide–induced mitochondrial dysfunction," *Journal of Clinical Biochemistry and Nutrition*, 22(2):113–123, 1997. Abstract from Datenbank BIOSIS bei STN:AN1997:4431146 BIOSIS, DN PREV 199799742349.

Thyagarajan et al., "Effect of *Phyllanthus Amarus* on Chronic Carriers of Hepatitis B Virus," *The Lancet*, Oct. 1, 1988, pp. 764–766.

Venkateswaran et al., "Effects of an extract from *Phyllanthus niruri* on hepatitis B and woodchuck hepatitis viruses: In vitro and in vivo studies," *Proc. Natl. Acad. Sci. USA*, vol. 84, pp. 274–278, Jan. 1987.

Thyagarajan et al., "In vitro inactivation of HBsAg by *Eclipta alba* Hassk and *Phyllanthus niruri* Linn," *Indian J Med Res* 76 (Suppl), pp. 124–130, Dec. 1982.

Syamasundar et al., "Antihepatotoxic principles of *Phyllanthus niruri* herbs," *J Ethnopharmacol* 14(1):41–4, Sep. 1985. Abstract from National Library of Medicine: IGM Full Record Screen.

del Barrio Alonso et al., "The in–vitro inactivation of HBsAg by extracts of plants in the genus Phyllanthus," *Rev Cubana Med Trop*., 47(2):127–130, 1995. Abstract from Nationa Library of Medicine: IGM Full Record Screen.

Doshi et al., "A two–stage clinical trial of *Phyllanthus amarus* in hepatitis B carriers: failure to eradicate the surface antigen," *Indian J Gastroenterol.*, 13(1):7–8, 1994. Abstract from National Library of Medicine: IGM Full Record Screen.

el–Mekkway et al., "Inhibitory effects of Egyptian folk medicines on human immunodeficiency virus (HIV) reverse transcriptase," *Chem Pharm Bull (Tokyo)*, 43(4):641–8, 1995. Abstract from National Library of Medicine: IGM Full Record Screen.

Wang et al., "Herbs of the genus Phyllanthus in the treatment of chronic hepatitis B: observations with three preparations from different geographic sites," *J Lab Clin Med.*, 126(4):350–2, Oct. 1995. Abstract from National Library of Medicine: IGM Full Record Screen.

Wang et al., "Efficacy of Phyllanthus spp. in treating patients with chronic hepatitis B," *Chung Kuo Chung Yao Tsa Chih.*, 19(12):750–1, 764, 1994. Abstract from National Library of Medicine: IGM Full Record Screen.

Powis et al., "High–performance liquid chromatographic assay for the antitumor glycoside phyllanthoside and its stability in plasma of several species," *J Chromatogr*, 342(1):129–34, Jul. 12, 1985. Abstract from National Library of Medicine: IGM Full Record Screen.

Efficacy Of *Phyllanthus Amarus* Treatment In Acute Viral Hepatitis, A,B and Non A Non B: An Open Clinical Trail—Indian J. Virol, vol. 13, No. 1, pp 59–64 (Jan. 1997).

Historical Treatment of Chronic Hepatitis B and Chronic Hepatitis C—P. Ferenci, Gut 1993; supplement; S69–S73.

* cited by examiner

Phyllanthus amarus (EtOH/H2O extract) inhibits iNOS expression

FIG. 12

Phyllanthus amarus (hexane extract) inhibits expression of COX-2

FIG. 13

Phyllanthus amarus (EtOH/H2O extract) inhibits expression of COX-2

FIG. 14

USE OF PHYLLANTHUS FOR TREATING CHRONIC INFLAMMATORY AND FIBROTIC PROCESSES

The present invention relates to the use of Phyllanthus for preventing or treating connective tissue proliferations, for maintaining the level of reduced glutathione, for inhibiting the lipopolysaccharide (LPS)-induced nitric oxide synthase (NOS) and for inhibiting the expression of the cyclooxygenase (COX-2) protein.

Phyllanthus embraces a widespread group of plants native to Central and South India, Taiwan, and areas of Central and South America. The term Phyllanthus means for the purpose of this invention all representatives of the botanical family of Phyllanthus, such as Phyllanthus niruri or, in particular, Phyllanthus amarus etc. The treatment of a large number of disorders with Phyllanthus is known in Indian folk medicine. Thus, for example, the author of "Doctor K. M. Nadkarni's Indian Materia Medica ($3^{rd}$ edition; revised and enlarged by A. K. Nadkarni)" reckons in volume I that the plant is known to be deobstruent, diuretic, astringent and cooling. Likewise, compositions with Phyllanthus are described for treating jaundice, dropsy, gonorrhoea, menorrhagia and other impairments of a similar type relating to the urogenital tract. Also known are the use of the sap from the trunk mixed with oil as ophthalmologicals or administrations for ulcers, wound sites and swellings etc., as well as the leaves for treating pruritus or other skin impairments.

There is also known to be a large number of active substances which can be isolated from Phyllanthus, phyllanthin, hypophyllanthin, triacontanol, triacontanal, repandusinic acid A (see, for example, JP 03206044 A; AIDS-Res-Hum-Retroviruses (11/1992), vol. 8 (11), HIV-1 reverse transcriptase . . . ), phyllanthostatin-1, phyllanthoside, phyllanthocin, phyllanthocin acid (see, for example, EP 173 4480; U.S. Pat. No. 4,388,457), phyllamycin A, B and C, retrojusticidin B, justicidin A and B (see, for example, AIDS-Weekly, 25.9.95, AIDS Therapies Extracts . . . ), linoleic acid, linolenic acid and ricinoleic acid (see, for example, Journal of the American Oil Chemists Society edition 81.06.00, ricinoleic acid in Phyllanthus niruri . . . ), phyllamyricin D, E and F, phyllamyricoside A, B and C (see, for example, J. Nat. Prod. (11/1996), vol. 59 (11), Six lignans from . . . ), putranjivain A (see, for example, Chem. Pharm. Bull. (Tokyo), (04/1995), vol. 43 (4), Inhibitory effects of Egyptian . . . ), ursulic acid and niruriside (see, for example, J. Nat. Prod. 02/96, vol. 59 (2), Niruriside, a new HIV . . . , Rec. Trav. Chim. (06/1996), Synthesis of . . . ).

Therapeutic effects and administrations disclosed to date are an age-retarding effect (see, for example, JP 08176004), prevention and therapy of immunodeficiencies such as AIDS, influenza, colds, tuberculosis, hepatitis, cirrhoses (see, for example, U.S. Pat. No. 5,529,778; AIDS-Weekly-Plus of 05.08.96, Antiviral (Drug Development); Inhibition of HIV . . . ), antineo-plastic effect (see, for example, U.S. Pat. No. 4,388,457), therapy of HIV, HBV and/or HCV infections, especially topical treatment of Kaposi's sarcoma (see, for example, EP 1734480; U.S. Pat. No. 5,466,455), effect as protease inhibitor, elastase inhibitor and as bleach (see, for example, JP 09087136), analgesic and antiinflammatory effect, effect as tyrosinase inhibitor (see, for example, JP 08012566) and a use as disinfectant in combination with extracts from other plants. Moreover, uses in cosmetic preparations are also known. It is evident from this large number of different areas of administration and isolated active substances that Phyllanthus is a thoroughly well-known group of medicinal plants employed for a large number of indications and complaints.

One pathological phenomenon which appears to be responsible for a large number of other complaints is so-called oxidative stress. By this is meant the stress on the living cell through accumulation of toxic oxidized compounds, such as lipid hydroperoxides, hydrogen peroxide, singlet oxygen and hydroxyl/superoxide anions. It is moreover possible for the stress to arise through free radicals which are produced locally or supplied from outside, especially so-called reactive oxygen species (ROS) or peroxonitrite free radicals etc. The oxidative stress can also be induced, for example, by exposure to radiation, xenobiotics, heavy metal ions or ischaemia/reperfusion (temporary interruption of the blood supply to an organ). In the latter case there is copious formation of superoxide anions by xanthine oxidase, one of the oxidases of about 300 kD and belonging to the flavoproteins, which catalyses the breakdown of purines, because its natural electron acceptor is oxygen. Under physiological conditions, these superoxide anions are deactivated by superoxide dismutase, but on reperfusion it has been demonstrated that this involves production of large amounts of oxygen free radicals.

Oxidative stress plays an important part in the development of a number of acute and, in particular, chronic disorders, for example inflammations of various types, microangiopathies, fibrosis, rheumatoid arthritis and other rheumatic disorders, arteriosclerosis (LDL oxidation), tumour development and progression, possibly Alzheimer's disease, but also drug-induced acute damage such as paracetamol damage to the liver.

The liver moreover plays, as central dynamic organ of the body, an important part in a large number of the physiological and microphysiological processes mentioned, the metabolic activities of the liver (intermediary metabolism) being of crucial importance on the one hand for supplying other organs but also, on the other hand, for the chemical conversion (biotransformation) of pharmaceutically active substances (see Pschyrembel, Klinisches W örterbuch, de Gruyter Verlag, 1986, pp. 935–937). The phenomenon of oxidative stress which has already been described is likewise for the most part combated by the body in the liver. This contains a reservoir of diverse reduced compounds of antioxidants, for example L-ascorbic acid, carotenoids, dihydrolipoic acid, uric acid, glutathione or α-tocopherol, and prevents the occurrence of reactive free radicals by means of various enzyme activities (for example superoxide dismutase, peroxidases such as glutathione peroxidase, catalase, etc.).

Oxidative stress also has in particular adverse effects on a large number of functions of liver tissue. Liver tissue frequently responds to this with connective tissue proliferation, which favours further progression of permanent liver damage, such as, for example, the development of a liver tumour. In this connection, bile acids in particular are involved in the pathogenesis of the hepatotoxic effect.

In all the above-mentioned disorders, the balance between oxidative stress and the defence systems of the cells and organs have crucial importance. It is therefore of crucial prophylactic and therapeutic importance on the one hand to protect the healthy liver from oxidative stress and, on the other hand, to strengthen the diseased liver so that it is able permanently to overcome pre-existing oxidative stress.

Compounds with a hepatoprotective activity have in some cases considerable disadvantages because they cannot be used if the liver is already diseased, because the toxicity is too high.

The present invention is therefore based on the object of providing substances which act on the liver and have both a prophylactic and a therapeutic effect.

The present invention relates to the use of Phyllanthus for preventing or treating connective tissue proliferations, in particular fibrotic changes for example of the liver, of the lung, of the kidney, of the pancreas, of the intestine, of endocrine organs, of the spleen, of the male or female urogenital tract, of the joints, for example as a consequence of chronic inflammatory processes such as, for example, rheumatoid arthritis or chronic cardiomyopathies, and of cirrhoses, an advanced stage of fibroses.

The use according to the present invention is therefore particularly preferable for fibroses and cirrhoses, preferably fibrosis of the liver and cirrhosis of the liver. In this connection in particular chronic inflammatory states lead to tissue atrophy and pronounced scar formation with progressive loss of function of the organs. An inhibition or prevention of the connective tissue proliferation therefore leads to less pronounced scar formation and retention of the ability of the organs to function.

The corresponding activity of Phyllanthus in preventing or improving in particular fibrosis of the liver presumably derives from an antioxidative effect, fibroses of the liver frequently being caused by viral infections. Thus, for example, all the known hepatitis viruses (hepatitis A, B, C, D, E and probably also G) have a pronounced tropism for liver cells. It is to be assumed that even the antiviral medicines currently used in medicine lead not to elimination of viruses but only to suppression of virus replication (virus suppression). Even if the virus disappears from the peripheral blood (below the detection limit), the virus is often still detectable in liver tissue. Thus, Phyllanthus can exert an advantageous effect on liver regeneration through its prophylactic and therapeutic effect. This contributes to reducing chronic inflammatory processes, with a reduction in the developing connective tissue proliferation in the liver. No medicines which can intervene in such an early step of degenerative development have yet been disclosed.

The present invention further relates to the use of Phyllanthus for maintaining the level of reduced glutathione. It has surprisingly been found that Phyllanthus extracts have potent activity in the maintenance of the level of reduced glutathione, which occurs in particular in the liver. In these experiments it was found that, in the functional cells of the liver (hepatocytes) showing increased lipid peroxidation due to t-butyl hydroperoxide, an extract of Phyllanthus not only suppresses further lipid peroxidation but even almost completely abolishes endogenous lipid peroxidation. In comparative experiments with untreated hepatocytes, a clear increase in the reductive capacity was found, which suggests improved maintenance of the intracellular level of reduced glutathione.

In preferred embodiments, Phyllanthus is used to reduce the expression of smooth muscle alpha-actin (SMA) mRNA and SMA protein. In a fibrotic liver, which has an increased rate of cell division, there is accumulation of extracellular matrix. The increased amounts of extracellular matrix are regarded as crucial for further progression of fibrosis of the liver as far as cirrhosis of the liver. The accumulation of extracellular matrix derives from activation of specific liver cells, the hepatic stellate cells (HSC), which in activated form are referred to as activated HSC. Compared with non-activated HSC, activated HSC produce larger amounts of smooth muscle alpha-actin (SMA) mRNA and protein, which is why the activation of HSC can be measured from the expression of SMA. The activation of HSC can also be judged from the expression and intracellular distribution of glial fibrillary acidic protein (GFAP). It has now been surprisingly found in a series of experiments that HSC lead, after treatment with Phyllanthus extracts, to distinctly smaller amounts of extractable SMA mRNA and SMA protein. Furthermore, by using immunofluorescence to detect the distribution of SMA and GFAP it could be demonstrated that extracts of Phyllanthus stabilise the normal phenotype of HSC and prevent the increase in cell size associated with their activated state. In addition, HSC treated with Phyllanthus extracts showed a distinct inhibition of cell growth, which underlines the activity of Phyllanthus extracts in these experiments. This means that there is a possibility of converting activated HSC as occur in fibrotic liver back into non-activated HSC, thus favouring a regression of fibrosis of the liver.

The present invention further relates to the use of Phyllanthus for inhibiting lipopolysaccharide (LPS)-induced nitric oxide synthase (NOS), particularly preferably inhibiting the induced nitric oxide synthase (iNOS), and the use of Phyllanthus for inhibiting the expression of cyclooxygenase (COX-2) protein.

LPS is a collective term for conjugates composed of lipid and polysaccharide portions. The LPS occurring in the outer membrane of the cell wall of Gram-negative bacteria are composed in principle of three components, namely lipid A, the core oligosaccharide and the O-specific side chains. Lipid A anchors the LPS in the bacterial cell wall and is also responsible for the immunoactivating effect of bacterial cell wall constituents.

The expression of iNOS and COX-2 can be induced in liver cells with the aid of LPS, which is why the stimulated cells can be used as model systems for fibrotic liver cells in which the expression of these two proteins is likewise raised. Both iNOS and COX-2 is known as a potent mediator of inflammatory processes like those occurring with degenerative changes of the liver. It has now surprisingly been found in comparative experiments that liver cells stimulated with LPS and then treated with Phyllanthus extracts showed a marked reduction in the rates of expression of the iNOS protein and the COX-2 protein.

This invention further comprises the use in one of the above-mentioned ways, using a fraction isolated from Phyllanthus. An isolated fraction means in this sense a subsidiary amount of Phyllanthus substances which has been removed, for example, by chromatographic means, distillation, precipitation, extraction, filtration or in other ways from Phyllanthus. It means in particular extracts and the fractions removed therefrom by chromatography, distillation, precipitation or extraction.

Another use according to the invention comprises uses in accordance with one of the above-mentioned examples, in which one or more chemical substances, in particular active substances, isolated from Phyllanthus are used. By these are meant in particular also single substances isolated from Phyllanthus extracts or other extracts, so-called natural substance isolates, as are also known, for example, from the prior art. The use of these isolated active substances has the advantage that it is generally necessary to use considerably smaller amounts of substance and, moreover, more specific effects are often achieved than with whole extracts or tablets.

In preferred uses according to one of the use forms according to the invention, Phyllanthus is selected from individual members of the Phyllanthus family, from the group of *Phyllanthus amarus, Phyllanthus niruri, Phyllanthus emblica, Phyllanthus urinaria, Phyllanthus myrtifolius* Moon, *Phyllanthus maderas pratensis* and/or *Phyllanthus ussuriensis.*

In the uses according to the invention it is possible to use leaves, bark, flowers, seeds, fruits, stalks, branches, trunk, root and/or wood of Phyllanthus, preferably the herb, that is to say all above-ground parts of the plant. It is moreover possible for Phyllanthus to be used in comminuted form and/or in unmodified form, that is to say as whole leaf, as granules, powder, precipitate, extract, dried extract and/or exudate, with extracts or dried extracts being preferred.

The preparation of Phyllanthus for the use according to the invention comprises the preparation of Phyllanthus powder or granules from one of the above-mentioned plant parts, extraction from plants, comminuted plant parts, powders, and residues which have already been treated previously with other solvents, with hexane, water, methanol and/or other alcohols. This also includes filtration and vacuum evaporation in order to obtain a dried extract. Another method comprises multiphase extraction with aqueous and/or alcoholic and/or polar solvents. Also usual is filtration, for example through cellulose filters, precipitation, preferably using ethanol, or separation by ultracentrifugation, and maceration. It is moreover always possible to operate at elevated or reduced temperatures.

It is particularly preferred here to use Phyllanthus in the form of an aqueous, lipophil or alcoholic extract, the alcoholic extract being carried out preferably with short-chain (C1 to C4) primary alcohols or mixtures thereof, especially methanol or ethanol, the lipophil one with C5–C10, branched or unbranched, chain hydrocarbons, or mixtures thereof, especially with n-hexane.

Also suitable as extractants are ethyl acetate or appropriate organic solvent/water mixtures, preferably methanol/water mixtures or ethanol/water mixtures. A suitable extraction process is disclosed, for example, in U.S. Pat. No. 4,673,575 or U.S. Pat. No. 4,937,074.

In uses according to the invention, Phyllanthus is preferably employed in the form of one or more medicinal products (see Römp, Lexikon Chemie, Version 1.4), such as an infusion solution, injection solution, tablet, granules, ointment, medicinal pack, enemas or in the form of one or more foodstuffs/food supplements. These embrace the usual medical and therapeutic applications and, in particular, also those as food supplements, it being possible to use Phyllanthus in these cases for prophylaxis and as functional antioxidant which is a natural and non-hazardous addition to foodstuffs and, moreover, shows the therapeutic and functional preventive effects mentioned.

The use of Phyllanthus in the uses according to the invention can take place orally, topically and/or parenterally.

In a preferred embodiment, one or more other active substances and/or suitable additives and/or auxiliaries are used in addition to Phyllanthus. The term active substance means for the purpose of this invention therapeutically active substances such as, for example, vitamin C or tocopherols, especially α-tocopherol, which are known as antioxidants or as active substances against oxidative stress, and, for example, anti-inflammatory substances. These also embrace therefore so-called combination products with Phyllanthus. It should also be noted in this connection in particular that the uses according to the invention are by no means confined to only one form, fraction or isolated active substance from Phyllanthus in each case, and it is also possible to use different forms and/or fractions and/or isolated active substance from Phyllanthus for a use.

Auxiliaries and additives mean for the purpose of this invention substances which are known to be added for therapeutic applications or as application for food supplements in order to permit or facilitate a corresponding use, for example adjuvants, disintegrants and lubricants, bulking agents, buffers, preservatives, stabilizers etc.

Fractions of Phyllanthus-derived material suitable for use in the methods of this invention may be obtained by dividing or extracting or fractionating Phyllanthus, including without limit leaves, bark, flowers, seeds, fruits, stalks, branches, trunk, root and/or wood, according to the fractionation procedures described above and in the Examples below. Individual procedures may be applied singly or in combination. Variations on these procedures will be apparent to the skilled artisan, in view of the guidance provided herein. Fractions of Phyllanthus may be formulated and adminstered as described herein for Phyllanthus material, including additives and/or auxiliaries. Preferably, fractions of Phyllanthus used in the methods of this invention will be biologically active as determined in one or more of the experimental procedures described herein for identifying and/or quantifying the biological effects of Phyllanthus, especially procedures described in the Examples. Selection of fractions which exhibit such biological activities is within the skill of the ordinary artisan in view of the guidance provided herein.

The following examples and figures are intended to describe the invention in detail without restricting it. These show.

EXAMPLE 1

Preparation of a Dried Extract According to the Invention (Fraction 1; Lot No.: 9810H)

2 kg of the herb of a Phyllanthus amarus cultivated in Madras, India, were converted into 450 g of powder. These 450 g of powder were extracted in a Soxhlet apparatus with 3 l of distilled n-hexane for 12 h. After filtration and vacuum evaporation, 25 g of dried n-hexane extract were obtained, the main constituents thereof being lipophilic lignans, sterols and pigments. The extract was a grey-brown paste which was insoluble in water and methanol and soluble in ethyl acetate.

EXAMPLE 2

Preparation of a Dried Methanol Extract
(Fraction 2; Lot No.: 9810M)

The remaining plant residue insoluble in n-hexane from Example 1 was successively extracted with 3 l of distilled methanol in a Soxhlet apparatus for 24 h. After filtration and vacuum evaporation, 50 g of dried methanol extract were obtained. The main constituents were flavonoids, oligomeric gallotannins and phenolcarboxylic acid. The dark-brown powder was insoluble in water and almost completely soluble in methanol.

EXAMPLE 3

Preparation of an Aqueous Supernatant
(Fraction 3; Lot No.: 9810Ws)

The methanol-insoluble plant residue (about 375 g) remaining after methanol extraction (see Example 2) was infused with 2.5 l of hot distilled water and then macerated cold (+4° C.) for 12 h. The warm water extract was filtered and then 2.5 l of ethanol (100% (=1:1)) were added dropwise in order to obtain a precipitate of the high molecular weight disaccharides and glycoproteins, which were then separated by ultracentrifugation at 7500 rpm. The lyophilized supernatant phase afforded 15 g of dry material. The main constituents were oligomeric gallotannins and other water-soluble polymers. The result was a reddish-brown powder which was soluble in water and insoluble in organic solvent.

EXAMPLE 4

Preparation of a Water Precipitate
(Fraction 4; Lot No.: 9810pp)

The ethanol-precipitated and centrifuged polymeric portions from Example 3 were dissolved in hot water and lyophilized. 5 g of extract are obtained starting from 450 g of crude powder. The main constituents are high molecular weight polysaccharides and glycoproteins. The resulting product was a brown powder which was insoluble in water.

EXAMPLE 5

Preparation of a Chlorophyll-free Methanol Crude Extract
(Fraction 5; Lot No.: 9901Mcf; P1159)

100 g of Phyllanthus powder from the herb were extracted with 500 ml of distilled methanol in a Soxhlet apparatus for 12 h. Filtration and vacuum evaporation resulted in 15 g of dried extract, which was dissolved in 300 ml of a hot mixture of distilled water and methanol in the ratio 1:1. The solution was reduced to half the volume on a water bath at 80° C., stirring occasionally. The oily precipitate was removed by hot (80° C.) filtration through cellulose paper. Hot distilled water (80° C.) was added to the filtrate to make up to 300 ml, followed by renewed filtration. Lyophilization of the filtrate afforded about 10 g of dry methanol extract. This had the appearance of a brown paste and was soluble in methanol.

EXAMPLE 6

Preparation of a Chlorophyll-free Water Extract
(Fraction 6; Lot No.: 9901Wcf)

50 g of Phyllanthus powder from the herb were extracted with 500 ml of distilled water on a water bath at 80–100° C. for 1 h, stirring occasionally. The hot solution was filtered through a cellulose paper. 100 ml of distilled methanol were added to the filtrate (about 400 ml). The mixture was evaporated to half the volume on a water bath at 80° C., stirring occasionally. The oily precipitate was removed by hot filtration (80° C.) through cellulose paper. Lyophilization of the filtrate afforded 3 g of dried water extract. This extract was a reddish-brown powder which was soluble in methanol.

EXAMPLE 7

Figure 1:
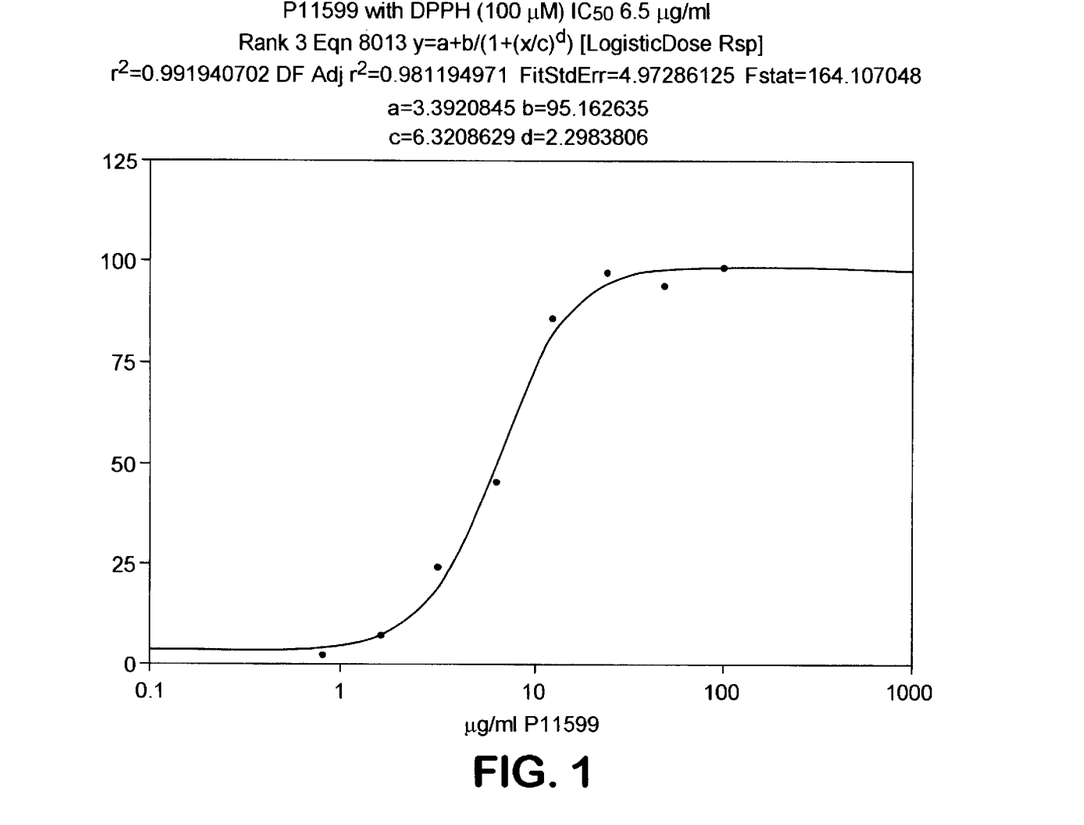
FIG. 1 the results of radical scavenger experiments with 1,1-diphenyl-2-picrylhydrazyl (DPPH) and the Phyllanthus extracts according to the invention.
Figure 2:
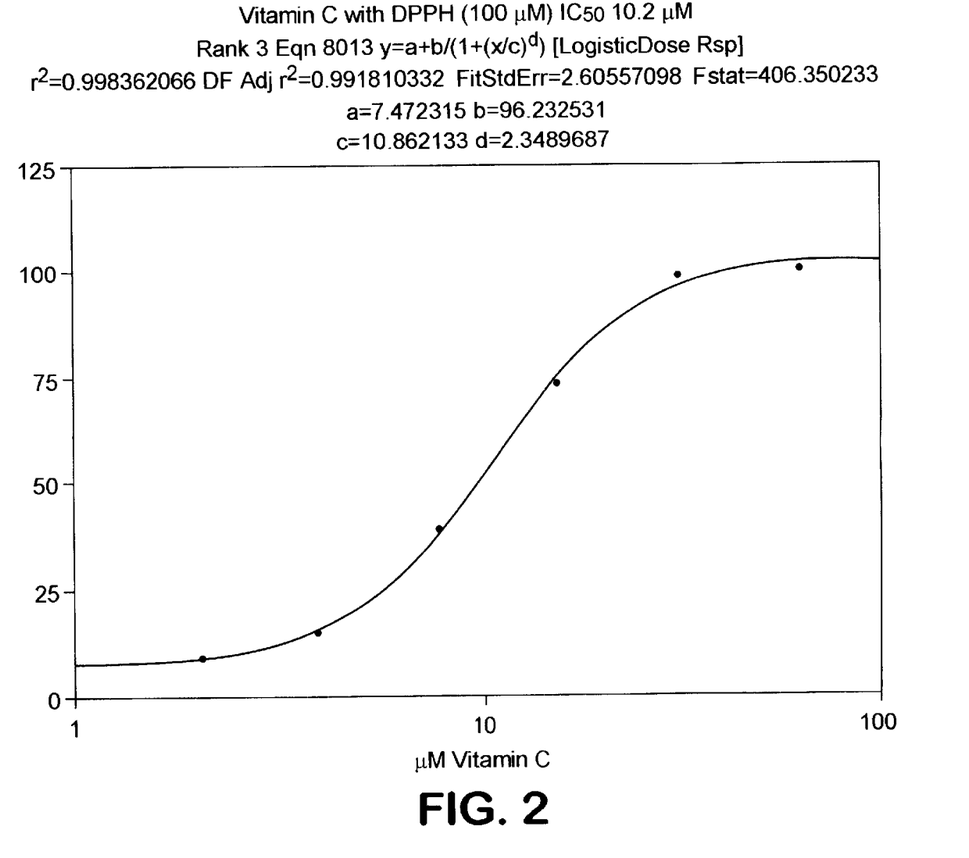
FIG. 2 the results of radical scavenger experiments with DPPH and vitamin C as comparison.
Figure 3:
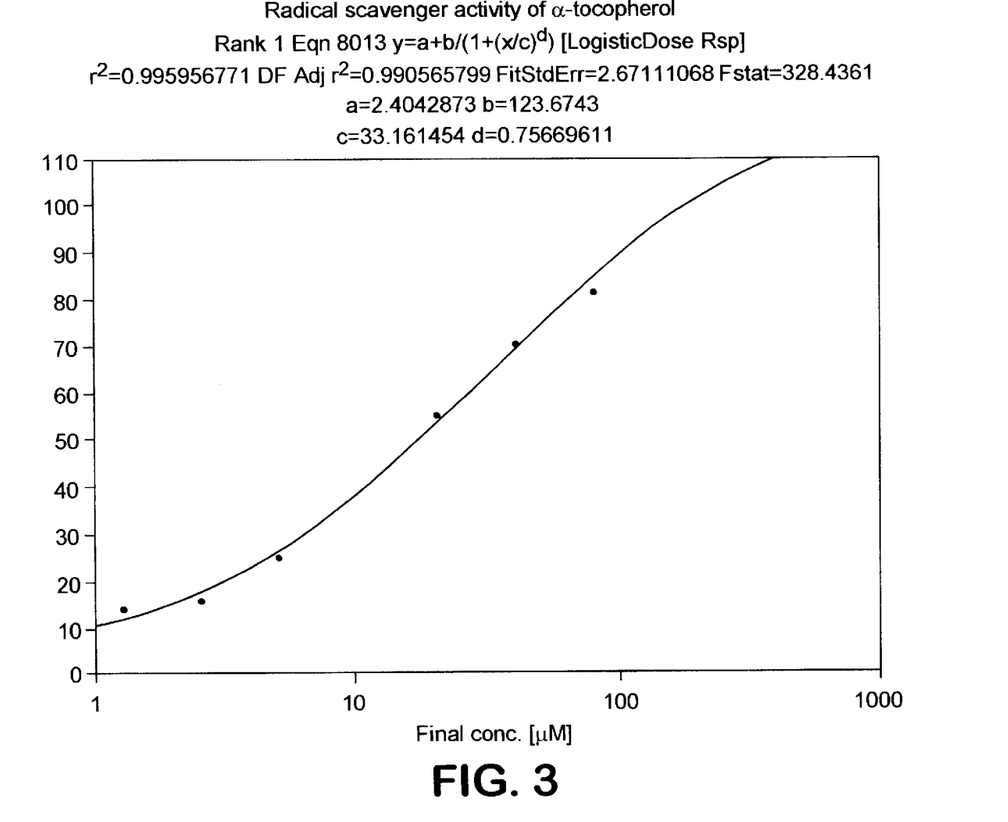
FIG. 3 the results of radical scavenger experiments with DPPH and α-tocopherol as comparison.

Radical Scavenger Experiment with DPPH 7 different concentrations of an extract according to the invention called P11599 from Example 5 were investigated for their ability to trap free radicals in a radical scavenger experiment. This was done by measuring the change in colour between a stable free radical DPPH (1,1-diphenyl-2-picrylhydrazyl) and the relevant nonradical 1,1-diphenyl-2-picrylhydrazine at 515 nm. This entailed incubating serial dilutions of the test substances in DMSO and duplicate determinations with a DPPH solution in methanol at 37° C. for 30 min and measuring the change in colour. The SC50, the concentration of sample at which 50% of the DPPH free radicals are trapped, was determined from the results. DMSO was used as negative control and ascorbic acid as positive control and these were measured—as was α-tocopherol too. Determination of the SC50 values gave 6.2 μg/ml for P11599, 10 μM for ascorbic acid and 18 μM for α-tocopherol (see FIGS. 1–3). As is evident from the plots and results, P11599 was a better free radical scavenger than α-tocopherol and as good as ascorbic acid.

EXAMPLE 8

Radical Scavenger Experiment with MTT

Figure 4:
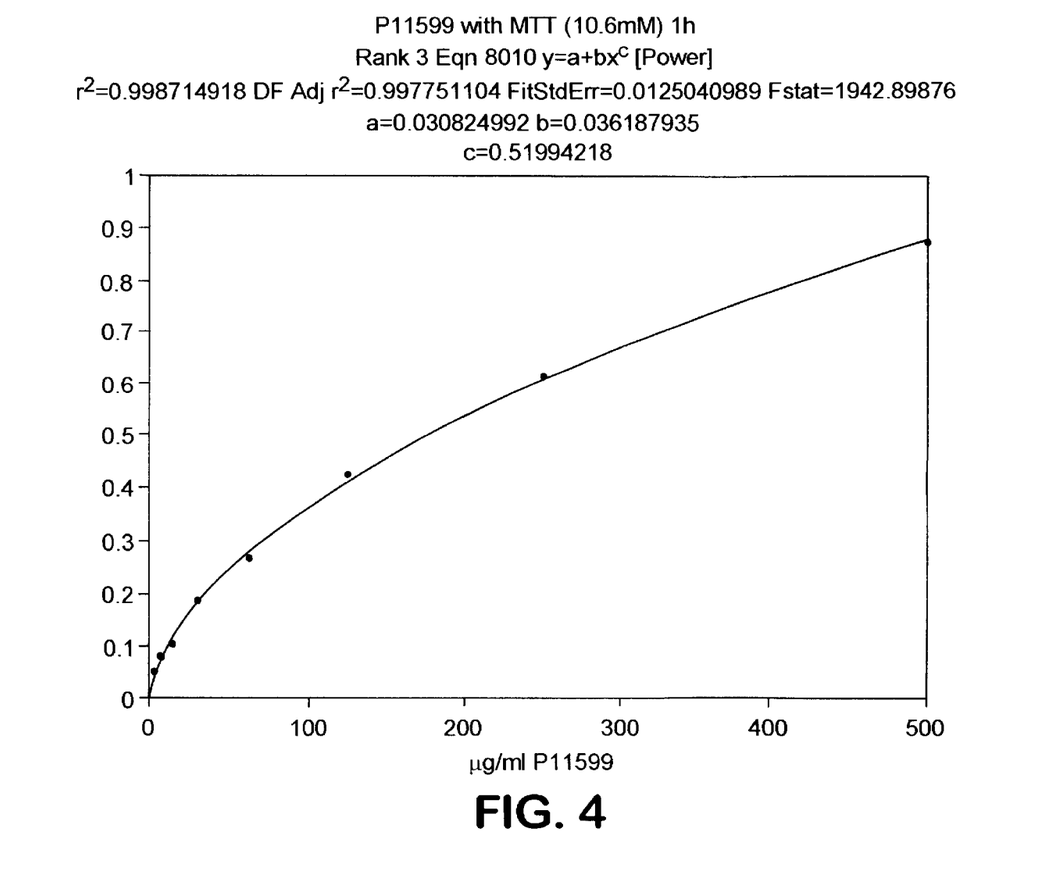
FIG. 4 the results of radical scavenger experiments with 3-[4,5-dimethylthiazol-2-yl]-2,5-di-phenyltetrazolium bromide (MTT) and the Phyllanthus extracts according to the invention.
Figure 5:
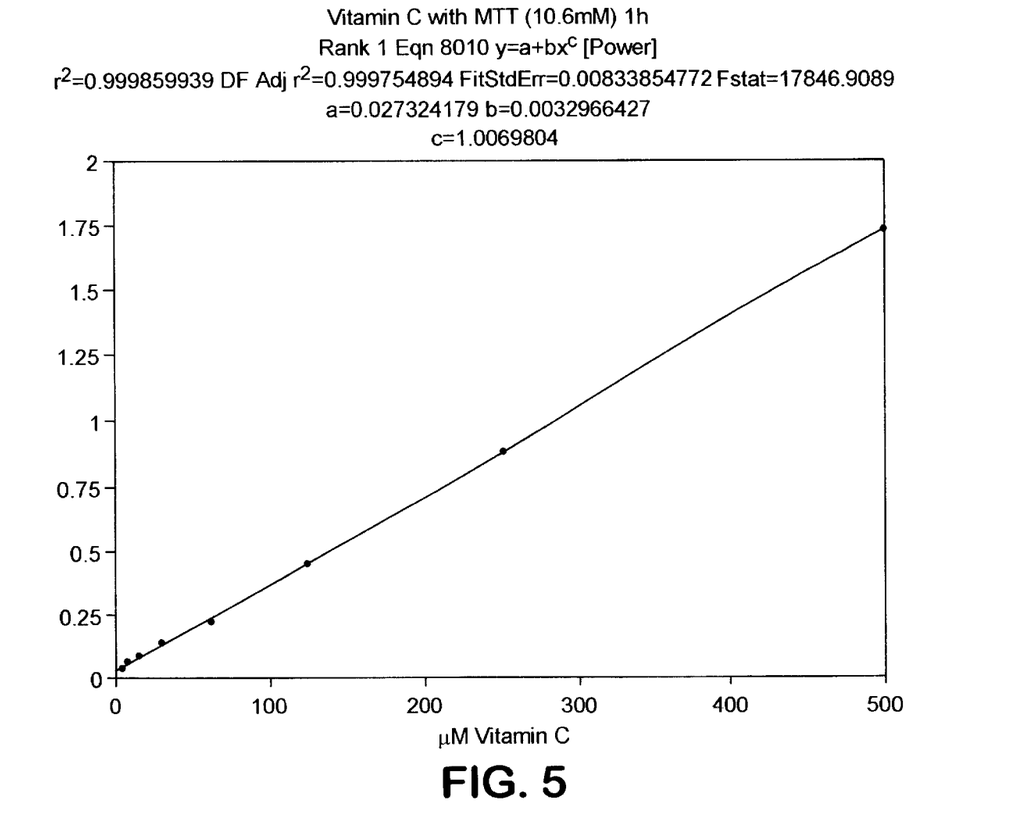
FIG. 5 the results of radical scavenger experiments with MTT and vitamin C as comparison.

MTT (3-[4,5-dimethylthiazol-2-yl]-2,5-diphenyltetrazolium bromide) was incubated in a concentration of 10.6 mM at 37° C. for 1 h with various concentrations of an extract P11599 according to the invention from Example 5 and with ascorbic acid as reference, and the change in absorption due to the action of the samples was determined by photometry. The result shows an extremely high antioxidant potential of P11599 similar to that of the relatively strong reducing agent ascorbic acid (see FIGS. 4 and 5).

EXAMPLE 9

Radical Scavenger Experiment with Cytochrome c

Figure 6:
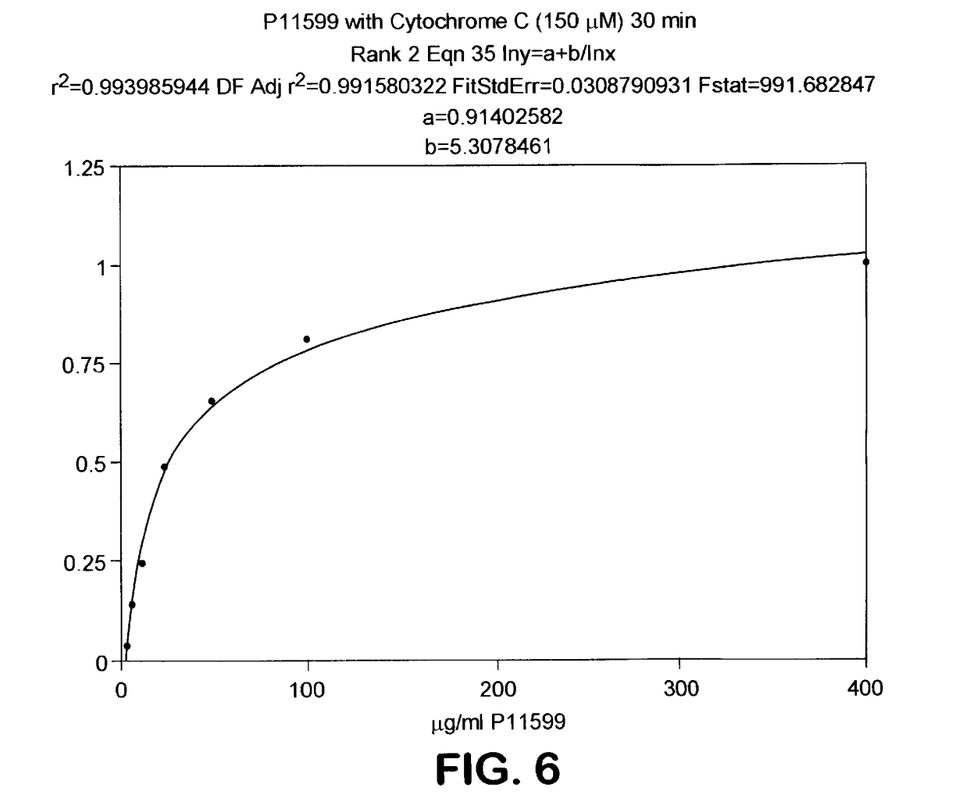
FIG. 6 the results of radical scavenger experiments with cytochrome and the Phyllanthus extracts according to the invention.
Figure 7:
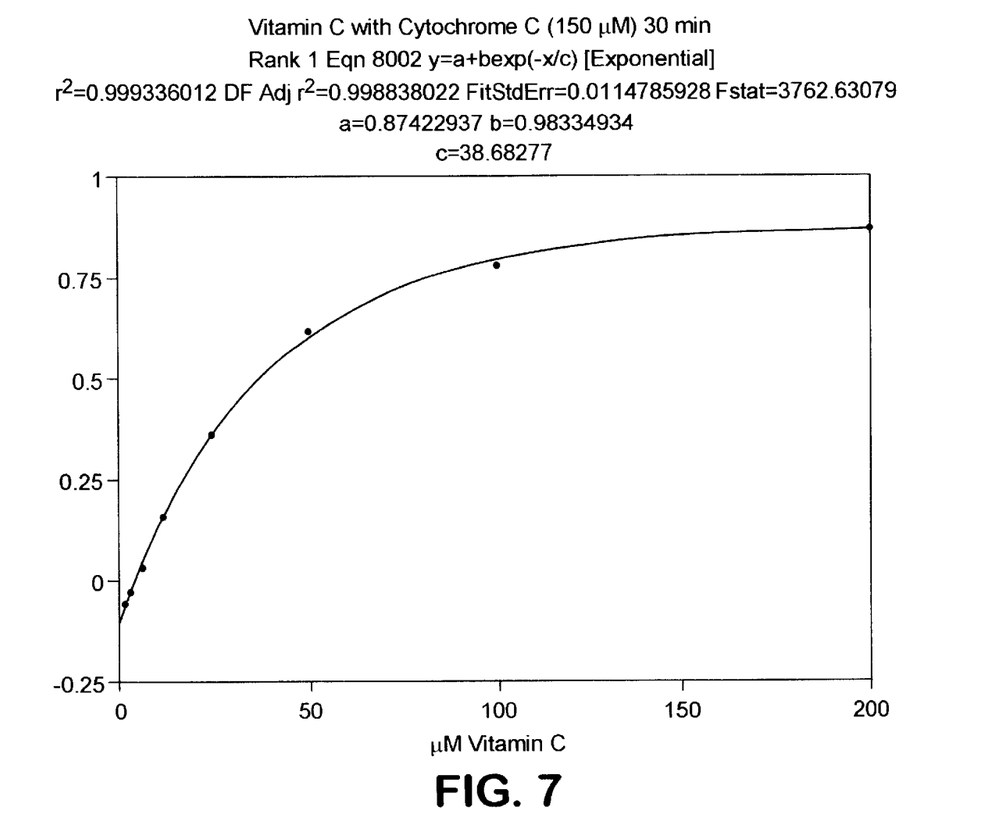
FIG. 7 the results of radical scavenger experiments with cytochrome and vitamin C as comparison.

Cytochrome c was incubated in a concentration of 150 μM at 37° C. for 0.5 h with various concentrations of an extract P11599 according to the invention from Example 5 and with ascorbic acid as reference, and the change in the absorption due to the action of the samples was determined by photometry. The result shows an extremely high antioxidant potential of P11599 similar to that of the relatively strong reducing agent ascorbic acid (see FIGS. 6 and 7).

EXAMPLE 10

Radical Scavenger Experiment with XTT/PMS

Figure 8:
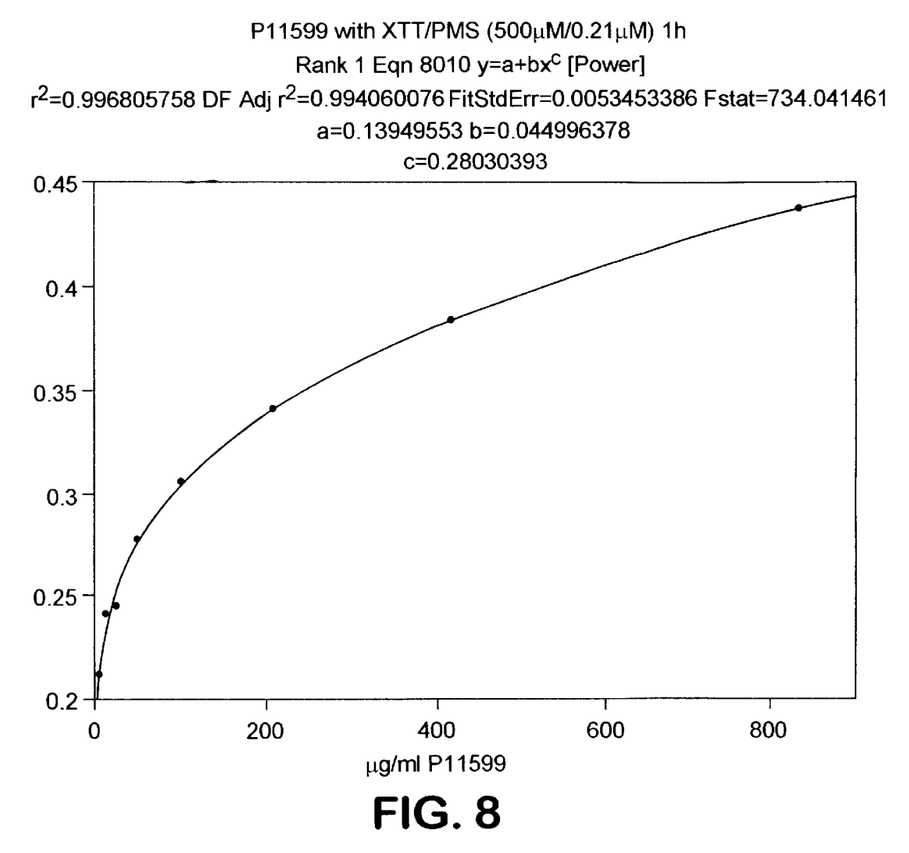
FIG. 8 the results of radical scavenger experiments with sodium 3,3'-[1- [(phenylamino)carbonyl]-3,4-tetrazolium]-bis(4-methoxy-6-nitro)benzenesulphonic acid hydrate/phenazine methosulphate (XTT/PMS) and the Phyllanthus extracts according to the invention.
Figure 9:
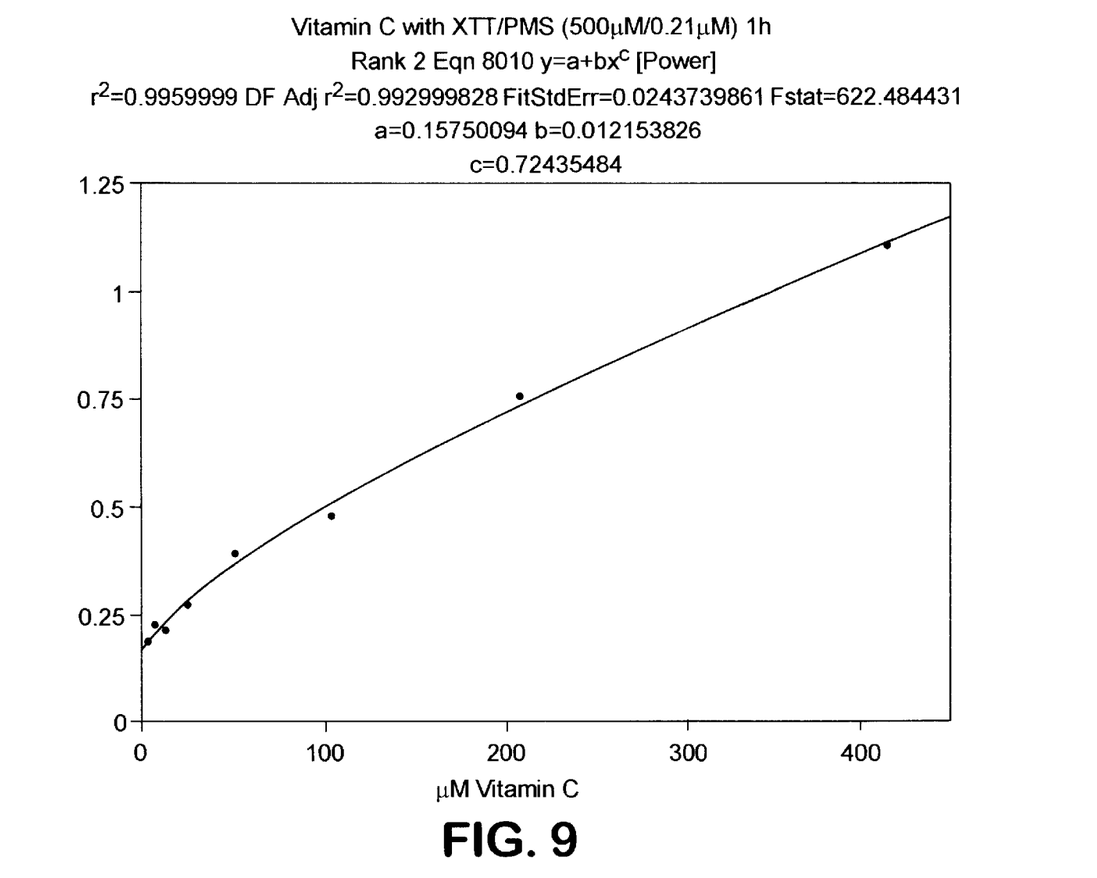
FIG. 9 the results of radical scavenger experiments with XTT/PMS and vitamin C as comparison.

XTT/PMS (sodium 3,3'-[1-[(phenylamino)carbonyl]-3,4-tetrazolium]-bis(4-methoxy-6-nitro)benzenesulphonic acid hydrate/phenazine methosulphate) was incubated in a concentration of 500 $\mu$M/0.2 l at 37° C. for 1 h with various concentrations of an extract P11599 according to the invention from Example 5 and with ascorbic acid as reference, and the change in absorption due to the action of the samples was determined by photometry. The result shows an extremely high antioxidant potential of P11599 similar to that of the relatively strong reducing agent ascorbic acid (see FIGS. 8 and 9).

EXAMPLE 11

Figure 10A:
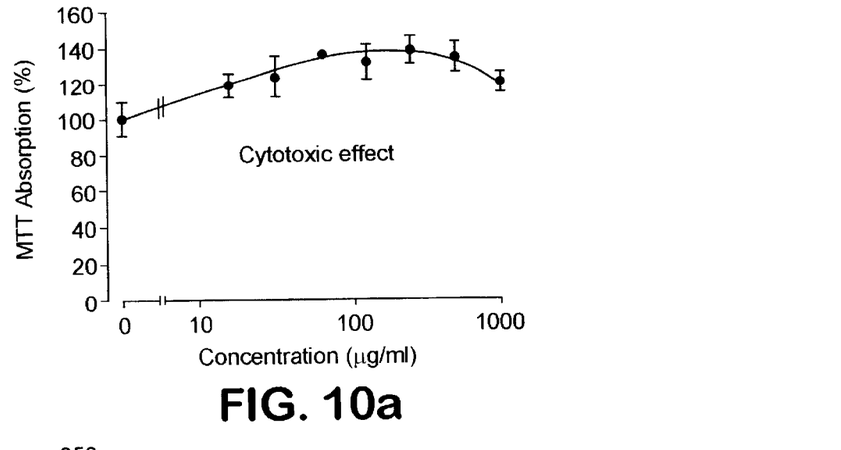
FIGS. 10a–c the effect of Phyllanthus extracts on liver cells (hepatocytes)
Figure 10B:
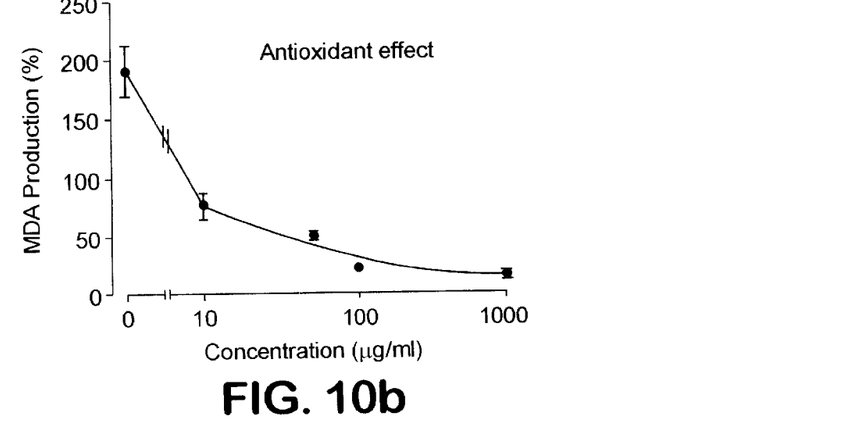
Figure 10C:
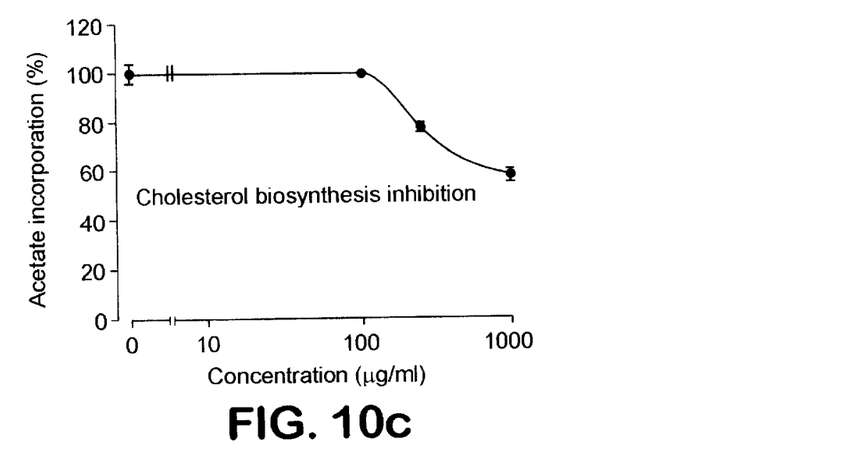
Figure 11A:
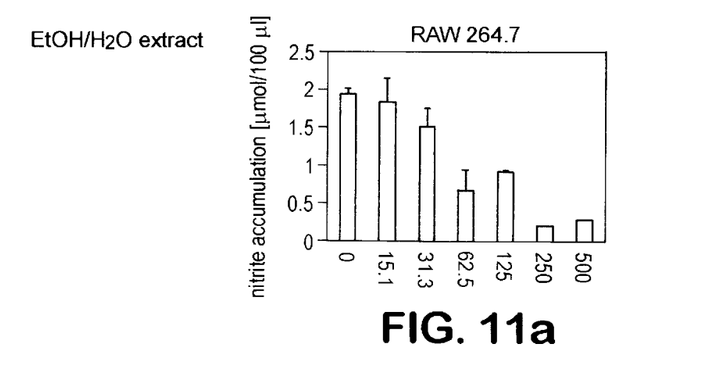
FIG. 11 the inhibiting effect of Phyllanthus extracts on the LPS-induced expression of NOS on the basis of reduced NO production.
Figure 11B:
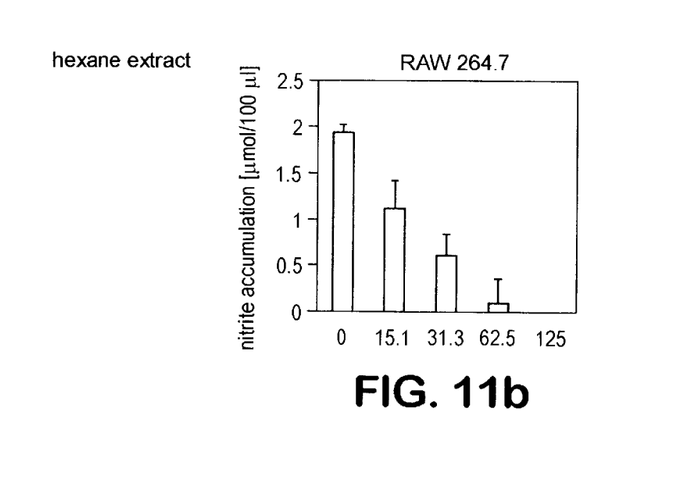
Figure 11C:
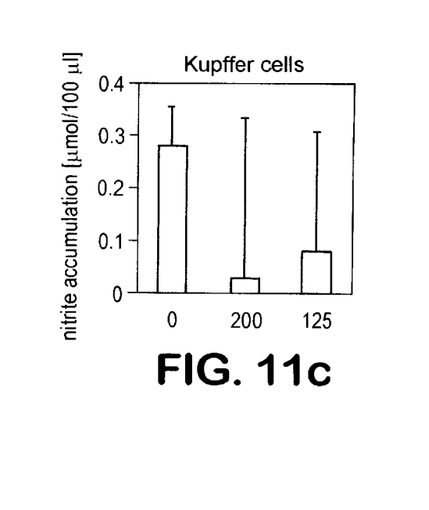
Figure 12:
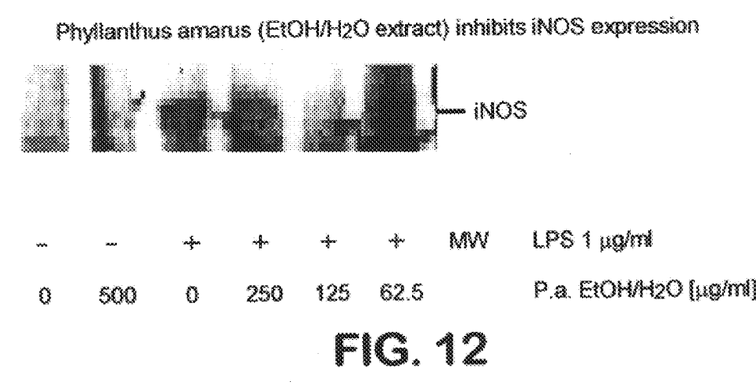
FIG. 12 the inhibiting effect of an ethanol/water extract of Phyllanthus on LPS-induced iNOS expression.
Figure 13:
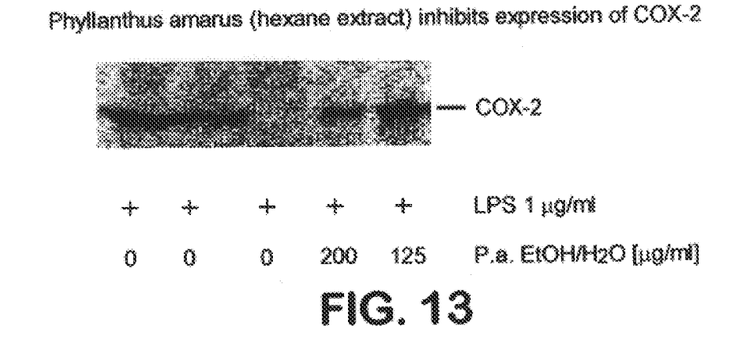
FIG. 13 the inhibiting effect of a hexane extract of Phyllanthus on LPS-induced COX-2 expression.
Figure 14:
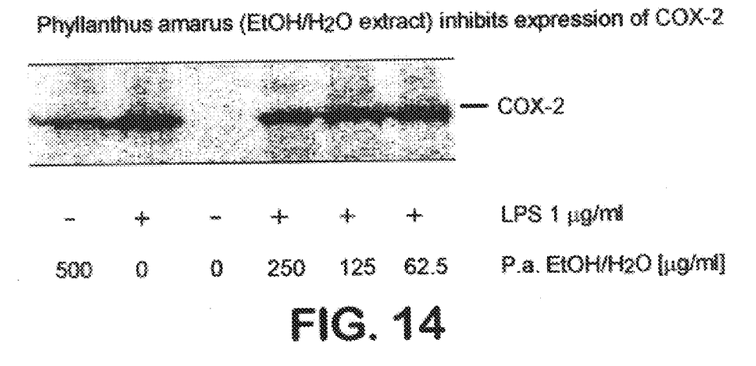
FIG. 14 the inhibiting effect of an ethanol/water extract of Phyllanthus on LPS-induced COX-2 expression.

Measurement of the Cytotoxic Effect and Influence on Reducing Capacity of the Cells The cytotoxic effect of an extract P11599 according to the invention from Example 5 was tested in various concentrations on cultivated rat hepatocytes in accordance with the experimental protocol of Gebhardt R. (1997) Toxicol. Appl. Pharmacol. 144, 279–286. No cytotoxic effect on hepatocytes was detectable—measured by the MTT absorption [%]—up to a concentration of 1 mg/ml (FIG. 10). A further surprising result shown by the rise in the curve in this experiment was that the effect of the extract according to the invention was in fact to increase the reductive capacity of the cells, which corresponds to an increase in the reducing capacity for maintaining the glutathione level (FIG. 10).

EXAMPLE 12

Measurement of the Reduction of Smooth Muscle Alphaactin (SMA) Expression

Resting hepatic stellate cells were obtained from a rat liver by perfusing the rat liver in situ with collagenase and Pronase. The hepatic stellate cells (HSC) were purified from the resulting cell suspension by a density gradient with Nycodenz™. The isolated HSC were then taken in cell culture (resting, non-activated phenotype). Under standard cultivation conditions in nutrient culture medium (DMEM, 18% fetal calf serum, usually purchasable from Sigma, Deisenhofen, Germany) there is spontaneous activation of the HSC (activated phenotype). For further activation, the HSC were passaged in cell culture. These cells were characterized morphologically and immunohistochemically as myofibroblastic HSC.

To carry out the actual series of tests, Phyllanthus extracts according to the invention (25% ethanol LAT No. 02700514, 50% ethanol LAT No. 0271614, 75% ethanol LAT No. 0272514) dissolved in DMSO were added in concentrations of 20 $\mu$g/ml, 60 $\mu$g/ml and 200 $\mu$g/ml to the nutrient culture medium of the activated HSC. The treated HSC were then incubated in nutrient culture medium for four days. After harvesting the HSC, total cellular RNA were isolated by conventional methods, and the concentration and quality thereof was determined by spectrophotometry and by agarose gel electrophoresis. Expression of the SMA mRNA was detected by the Northern blot method known in the state of the art.

With all the tested Phyllanthus extracts, addition of 200 $\mu$g/ml led to distinct inhibition of the growth of HSC in cell culture and a considerably smaller amount of isolated total cellular RNA. In the Northern blot there was likewise observed to be a distinct reduction in the expression of the SMA mRNA, which was evident on use of the 50% ethanol extract at a concentration as low as 60 $\mu$g/ml.

EXAMPLE 13

Measurement of the Reduction of the Expression of LPS Induced Nitric Oxide Synthase (NOS), of the Induced NOS Protein (iNOS) and of the Cyclooxygenase (COX-2) Protein Nitric oxide (NO) production effected by NOS was measured using macrophages which were incubated in RPMI nutrient culture medium with 10% fetal calf serum (usually purchasable from Sigma, Deisenhofen, Germany). The cells were then stimulated with LPS (1 $\mu$g/ml) and incubated with or, as a control, without Phyllanthus extracts for 24 h. The NO concentration was determined by the Griess assay (Kiemer, A. and Vollmar, A. (1998), J. Biol. Chem. 273 (22): 13444–13451).

NO production was effectively reduced with the tested Phyllanthus extracts, especially by a hexane extract (LAT No. 01600514) at a concentration 12.5 $\mu$g/ml and an ethanol/water extract (LAT No. 00690514) in a concentration of 250 $\mu$g/ml. A reduction in the LPS-induced iNOS and COX-2 protein expression was found at concentrations of 125 $\mu$g/ml hexane extract and ethanol/water extract (FIGS. 11–14).

For purposes of clarity of understanding, the foregoing invention has been described in some detail by way of illustration and example in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in medicine, immunology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference. Likewise, German patent application Ser. No. 199 19 585.4, filed Apr. 29, 1999, from which priority is claimed, is also incorporated herein by reference in its entirety.

What is claimed is:

1. A method for treating connective tissue proliferation comprising administration of a composition comprising *Phyllanthus amarus* or a fraction thereof to a patient whereby proliferation of connective tissue in the patient is reduced.

2. The method according to claim 1, wherein the expression of smooth muscle alpha-actin (SMA) and/or glial fibrillary acidic protein (GFAP) mRNA is reduced.

3. The method according to claim 1, wherein the expression of SMA and/or GFAP protein is reduced.

4. The method according to claim 3, wherein the reduction of SMA and/or GFAP expression takes place in hepatic stellate cells (HSC).

5. The method according to claim 4, wherein activated HSC are converted into non-activated HSC.

6. The method of claim 1, wherein said connective tissue proliferation comprises fibrosis or cirrhosis.

7. The method of claim 6, wherein said fibrosis or cirrhosis comprises fibrosis or cirrhosis of the liver.

8. The method according to claim 1, wherein a fraction isolated from *Phyllanthus amarus* is used.

9. The method according to claim 1, wherein one or more active substances isolated from *Phyllanthus amarus* are used.

10. The method according to claim 1, wherein leaves, bark, flowers, seeds, fruits, stalks, branches, trunk, root, the herb portion of *Phyllanthus amarus*, or mixtures or combinations thereof, are used.

11. The method according to claim 1, wherein the *Phyllanthus amarus* is used in comminuted form and/or in unmodified form as granules, powder, precipitate, extract, dried extract and/or exudate.

12. The method of claim 11, wherein the *Phyllanthus amarus* is an extract or dried extract.

13. The method according to claim 12, wherein the *Phyllanthus amarus* is an extract of one or more aqueous solvents, nonpolar solvents, alcohol solvents or mixtures thereof.

14. The method according to claim 13, wherein the one or more solvents comprise n-hexane.

15. The method according to claim 1, wherein the administration takes place in the form of an infusion solution, injection solution, tablet, granules, ointment, enema, medicinal pack or food supplement.

16. The method according to claim 1, wherein administration takes place orally, topically or parenterally.

17. The method according to claim 1, wherein other active substances in addition to *Phyllanthus amarus* are administered in combination with suitable additives and/or auxiliaries.

18. The method according to claim 17, wherein ascorbic acid, tocopherols, or both are co administered.

19. A method of reducing fibrosis of hepatic tissue comprising administering to a patient in need thereof an amount of a composition comprising *Phyllanthus amarus* or a fraction thereof sufficient to inhibit expression of smooth muscle alpha-actin (SMA), glial fibrillary acidic protein (GFAP), or both.

20. A method for treating connective tissue proliferation comprising administration of Phyllanthus or a fraction thereof to a patient whereby proliferation of connective tissue in the patient is reduced, wherein said Phyllanthus is an extract of one or more aqueous solvents, nonpolar solvents, alcohol solvents or mixtures thereof, and wherein the one or more solvents comprise ethanol or methanol, wherein the Phyllanthus comprises an ethanol/water extract of the leaves of *Phyllanthus amarus* and said extract is administered orally.

21. A method for treating connective tissue proliferation comprising administration of a composition comprising an ethanol/water extract of *Phyllanthus niruri* or a fraction thereof to a patient whereby proliferation of connective tissue in the patient is reduced.

22. The method according to claim 21, wherein the expression of smooth muscle alpha-actin (SMA) and/or glial fibrillary acidic protein (GFAP) mRNA is reduced.

23. The method according to claim 21, wherein the expression of SMA and/or GFAP protein is reduced.

24. The method according to claim 23, wherein the reduction of SMA and/or GFAP expression takes place in hepatic stellate cells (HSC).

25. The method according to claim 24, wherein activated HSC are converted into non-activated HSC.

26. The method of claim 21, wherein said connective tissue proliferation comprises fibrosis or cirrhosis.

27. The method of claim 26, wherein said fibrosis or cirrhosis comprises fibrosis or cirrhosis of the liver.

28. The method according to claim 21, wherein a fraction isolated from *Phyllanthus niruri* is used.

29. The method according to claim 21, wherein one or more active substances isolated from *Phyllanthus niruri* are used.

30. The method according to claim 21, wherein leaves, bark, flowers, seeds, fruits, stalks, branches, trunk, root, the herb portion of *Phyllanthus niruri*, or mixtures or combinations thereof, are used.

31. The method according to claim 21, wherein the *Phyllanthus niruri* is used in comminuted form and/or in unmodified form as granules, powder, precipitate, extract, dried extract and/or exudate.

32. The method of claim 31, wherein the *Phyllanthus niruri* is an extract or dried extract.

33. The method according to claim 21, wherein the administration takes place in the form of an infusion solution, injection solution, tablet, granules, ointment, enema, medicinal pack or food supplement.

34. The method according to claim 21, wherein administration takes place orally, topically or parenterally.

35. The method according to claim 21, wherein other active substances in addition to *Phyllanthus niruri* are administered in combination with suitable additives and/or auxiliaries.

36. The method according to claim 35, wherein ascorbic acid, tocopherols, or both are co administered.

37. A method of reducing fibrosis of hepatic tissue comprising administering to a patient in need thereof an amount of a composition comprising an ethanol/water extract of *Phyllanthus niruri* or a fraction thereof sufficient to inhibit expression of smooth muscle alphaactin (SMA), glial fibrillary acidic protein (GFAP), or both.

* * * * *